(12) United States Patent
Henry et al.

(10) Patent No.: US 7,985,382 B1
(45) Date of Patent: Jul. 26, 2011

(54) MOBILE ALL HAZARDS RECEIPT FACILITY/ANALYTICAL LABORATORY

(75) Inventors: Charles E. Henry, Joppa, MD (US);
George J. Noya, Bel Air, MD (US); Luis E. Faure, Abingdon, MD (US); Monica J. Heyl, Joppa, MD (US); Dennis J. Reutter, Havre de Grace, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1040 days.

(21) Appl. No.: 11/751,839

(22) Filed: May 22, 2007

Related U.S. Application Data

(60) Provisional application No. 60/809,494, filed on May 31, 2006.

(51) Int. Cl.
*B01J 19/00* (2006.01)
*A61L 2/00* (2006.01)
*A61L 2/18* (2006.01)
*A61L 9/00* (2006.01)

(52) U.S. Cl. ........... 422/291; 422/292; 422/295; 422/28

(58) Field of Classification Search .................. 422/291, 422/292, 295, 28; 296/24.32, 24.4; 600/21
See application file for complete search history.

(56) References Cited

U.S. PATENT DOCUMENTS

| | | | | |
|---|---|---|---|---|
| 3,350,127 | A * | 10/1967 | Hekelaar | 292/251.5 |
| 4,667,580 | A * | 5/1987 | Wetzel | 454/187 |
| 5,152,814 | A * | 10/1992 | Nelson | 96/224 |
| 5,342,121 | A * | 8/1994 | Koria | 312/1 |
| 5,828,303 | A * | 10/1998 | Williams | 340/545.1 |
| 5,921,191 | A * | 7/1999 | Gabel | 109/7 |
| 6,394,523 | B1 * | 5/2002 | Yoo et al. | 296/24.32 |
| 6,595,247 | B1 * | 7/2003 | Landy et al. | 141/97 |
| 2003/0071543 | A1 * | 4/2003 | Daghighian | 312/1 |
| 2003/0138344 | A1 * | 7/2003 | Mielnik et al. | 422/2 |
| 2004/0058637 | A1 * | 3/2004 | Laiti | 454/229 |
| 2004/0201239 | A1 * | 10/2004 | Pellegrin, Jr. | 296/24.38 |
| 2006/0107635 | A1 * | 5/2006 | Homan et al. | 55/385.2 |
| 2009/0047173 | A1 * | 2/2009 | Mielnik et al. | 422/28 |

FOREIGN PATENT DOCUMENTS
WO  WO 03/095765  * 11/2003

* cited by examiner

*Primary Examiner* — Sean E Conley
*Assistant Examiner* — Regina Yoo
(74) *Attorney, Agent, or Firm* — Ulysses John Biffoni

(57) ABSTRACT

A mobile All Hazards Receipt Facility (AHRF) is provided in an enclosure suitable for mounting on a base vehicle such as a semi-trailer. The AHRF includes a containment area compliant with BSL-3 standards, a containment area compliant with BSL-2 standards, a unique bleaching/decontamination station having an airlock to the outside for receiving incoming sample containers, a class III Biosafety Cabinet (Glovebox) connected to the bleaching station via an airlock through which samples are passed for processing, a biosafety cabinet as well as an onboard air handling system that provides air conditioning, filtration and exhaust and maintains appropriate BSL-2 and BSL-3 air pressure differentials.

13 Claims, 3 Drawing Sheets

MOBILE ALL HAZARDS RECEIPT FACILITY/ANALYTICAL LABORATORY

CROSS-REFERENCE TO RELATED APPLICATIONS

This application claims the benefit of priority from U.S. Provisional Patent Application Ser. No. 60/809,494, filed on May 31, 2006.

GOVERNMENT INTEREST

The invention described herein may be manufactured, licensed, and used by or for the U.S. Government.

TECHNICAL FIELD

The present invention relates in general to screening and assessment of samples that may contain chemical, biological, radiological, highly-explosive residue, or toxic industrial materials, and more particularly to a self contained mobile all hazards receipt and containment facility to perform, rapid and safe screening and assessment of a wide variety of samples to determine whether they may contain chemical, biological, radiological, highly-explosive residue, or toxic industrial materials.

BACKGROUND

During the period following Sep. 11, 2001 and the anthrax releases that occurred shortly thereafter, public health laboratories in the U.S. became severely overloaded with potentially harmful specimens of many descriptions that needed to be assessed and identified rapidly. While HAZMAT teams and other resources were helpful in many cases in assessing radiological and explosive hazards, most public health laboratories lacked the training and equipment to cover and contain a broad range of chemical and biological hazards. This lack of expertise and equipment presented a high level of uncertainty and anxiety for laboratory personnel who received samples and had no way of knowing how hazardous they were. Such uncertainty and the very real potential for harm to personnel and consequent massive loss of laboratory capacity has strengthened the demand for a standardized approach to specimen receiving, triage, and assessment under conditions that will protect each laboratory facility and its staff while also ensuring the integrity of forensic evidence and preserving a legally defensible chain-of-custody. Embodiments according to the present invention are designed to address at least the foregoing needs.

SUMMARY

In general, in one aspect, an embodiment of a mobile hazards receipt analytical laboratory includes a platform suitable for mounting on a base vehicle, a substantially sealed enclosure mounted on or integrated with the platform for containing laboratory equipment and personnel, the enclosure comprising a plurality of sealed outside entries that can be locked to prevent unauthorizd access. The enclosure further includes an anteroom maintained at a positive pressure of about +0.10 in wg with respect to the outside air that leads to at least one other room in the laboratory and comprises a main outside entry, a containment area compliant with BSL (Biosafety Level)-2 standards, maintained at a negative pressure of about −0.10 in wg with respect to the outside air, which is directly accessible from the anteroom, a containment area compliant with BSL-3 standards, maintained at a negative pressure of greater than about −0.25 in wg with respect to the outside air, which is directly accessible from the change room, a bleaching station located in the BSL-2 area, the bleaching station comprising a partially enclosed work area for application of a decontamination solution to sample containers, wherein said bleaching station further comprises a HEPA and carbon filtered exhaust system; and a double-sided class III glovebox located in the BSL-3 area, the glovebox comprising a CBR exhaust air filtration system, an airlock through which samples may be passed directly from the bleaching station, and a second airlock through which samples can be passed into a biosafety cabinet.

In general, in another aspect, an embodiment of an air handling system for a mobile laboratory which includes a BSL-2 compliant area and a BSL-3 compliant area, includes a first air supply and exhaust system that provides HEPA air supply and HEPA carbon filtered single-pass air exhaust and at least 30 outside air exchanges per hour to the BSL-3 level containment area of the mobile laboratory and a second air supply and exhaust system that provides HEPA and carbon filtered air that may be recirculated, at least in part, and that provides at least 10 outside air changes per hour to a BSL-2 level containment area of the mobile laboratory.

In yet another aspect, a method of receiving and processing samples through a mobile hazards receipt facility includes receiving a sample into the mobile hazards receipt facility at a double door airlock, accepting the sample according to a two-man entry rule and passing the sample directly from the double door airlock into a bleaching station located in a BSL-Biosafety Level 2 confinement area, decontaminating any secondary overpacking of the sample in the bleaching station, removing any secondary overpacking of the sample to reveal a primary sample container and decontaminating a second time, passing the sample from the bleaching station through a double-door airlock into a glovebox that meets or exceeds standards for a Class III Biological Safety Cabinet, opening the sample container in a glovebox, performing triage on the sample in the glovebox, passing the sample from the glovebox into a quad-door airlock leading from the glovebox to a Class II A2 biosafety cabinet (according to Standard NSF-49), performing additional analysis of the sample in the biosafety cabinet, if needed, re-packing the sample for transport to another facility, and passing the re-packed sample out of the mobile hazards receipt facility through a double door airlock.

DETAILED DESCRIPTION

Figure 1:
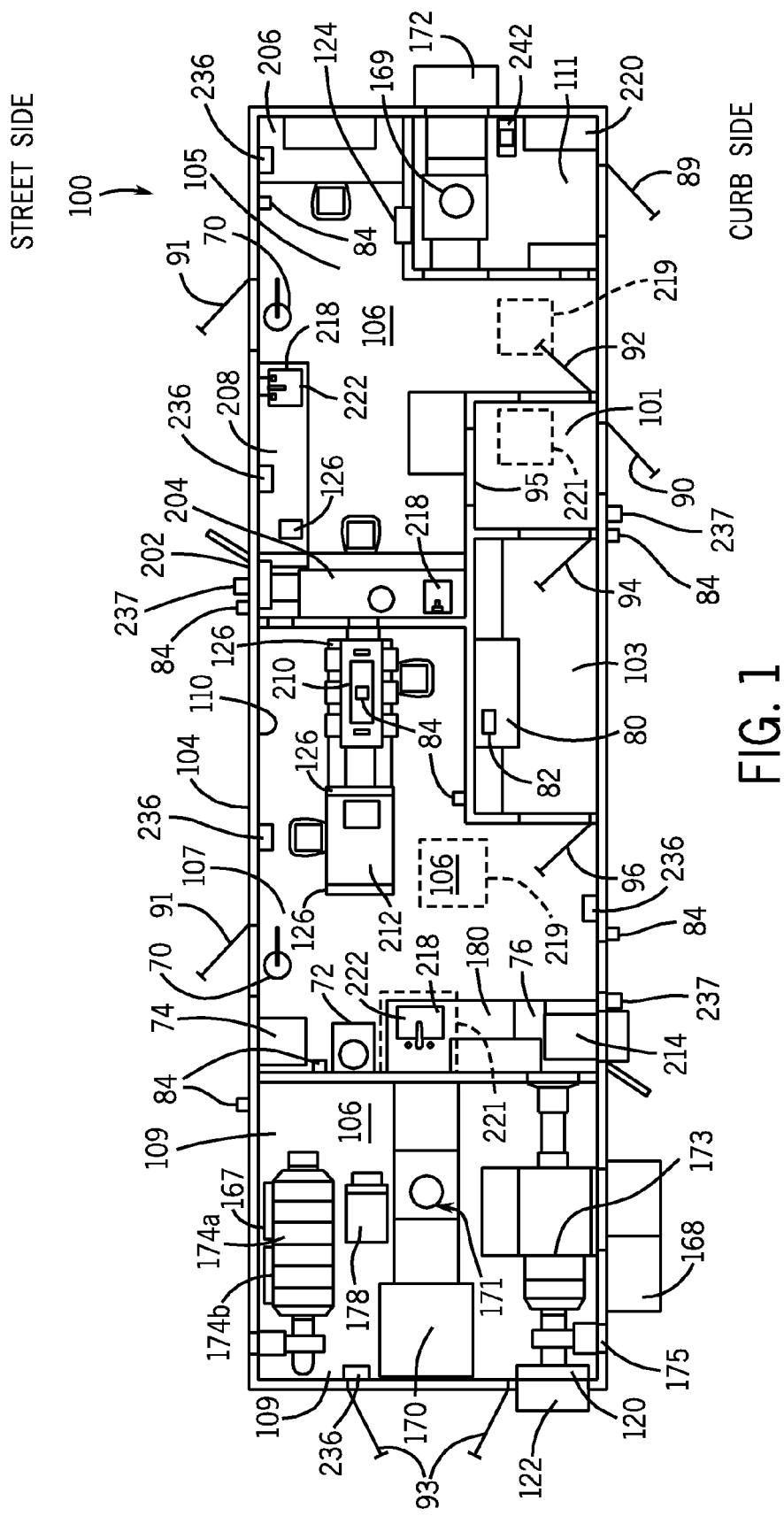
FIG. 1 shows a simplified top schematic view of a preferred embodiment of a mobile hazards receipt facility according to the present invention.

In the following detailed description, reference is made to the accompanying drawings. The drawings are a part of this disclosure and illustrate specific embodiments in which the invention, as claimed, may be practiced. The invention, however, may be embodied in many different forms and should not be construed as limited to the embodiments set forth; rather, these embodiments are provided so that this disclosure will be thorough and complete, and will fully convey the scope of the invention to those skilled in the art. As will be appreciated by those of skill in the art, the present invention may be embodied in methods, systems and devices. Wherever possible, the same reference numbers will be used throughout the drawings to refer to the same or like parts.

In general, a mobile hazards receipt analytical laboratory (variously referred to as an "All Hazards Receipt Facility," "AHRF" or "Hazards Receipt Facility" in this document) should be built on a base vehicle that is small enough to be readily transportable but still be large enough to accommodate a working laboratory environment that provides all necessary analytical and containment equipment. The base vehicle selected in the preferred embodiment is a wheeled, semi-trailer, transportable over most major roads, and which may be hauled and positioned next to a fixed site facility such as a public health laboratory. The AHRF thus may be operated as a semi-permanent structure in communication with a fixed site laboratory facility. It should also be noted the term "AHRF" as used herein is not intended to mean literally that "all" hazards can be received by such a laboratory.

Embodiments of AHRF according to the present invention are designed to incorporate true Biosafety Level 3 (BSL-3) facilities in accordance with guidelines established by "Biosafety in Biomedical and Microbiological Laboratories" (BMBL), 4th Edition, May 1999, incorporated by reference herein as if fully set forth. "BSL-3" is one of four classifications for biologic research designated by the U.S. Centers for Disease Control and Prevention. The levels—1 through 4—signify the increasing level of risk to humans from pathogens and call for increasingly stringent precautions and safeguards to protect both people working inside a containment facility and members of the public on the outside.

As would be familiar to those of skill in the art, a number of design considerations apply to any BSL-3 facility and are incorporated by reference as if fully set forth in embodiments of AHRFs according to the present invention. These include, but are not limited to, surrounding the facility with a perimeter wall and isolating the building from random, adjacent traffic, providing video cameras and other surveillance equipment, controlling ingress and egress and providing biologically sealed doors. The facility should be designed to minimize the risk that air and airborne contaminants inside the containment areas may escape to the outside and be equipped with redundant state-of-the-art monitoring systems. Additionally, containment areas of the facility should be configured to provide a negative air pressure barrier, i.e., inside air pressure is less than ambient air pressure so that any air leaks will result in an airflow into the facility from the outside. Engineering of the airflow, containment and sample movement are at the heart of embodiments of AHRFs according to the present invention.

Overall Construction Features

FIG. 1 shows a first and preferred embodiment of an AHRF 100 according to the present invention. AHRF 100 is contained on a base vehicle (not shown). The base vehicle is preferably a conventional 48 ft (L)×13 ft 9 in (W)×13 ft 6 in (H) semitrailer weighing approximately 45,000 lb. In general, the base vehicle is dimensioned to be large enough to carry an AHRF facility and still be transportable by conventional semi-tractor over most major roads, including the US Interstate Highway system, in accordance with US DOT regulations. To maintain a mobile capability, the number of axles on the base vehicle should be as few as possible. In this instance, if only two axles are used, each axle would have to be rated to over 15,000 lbs. This configuration generally would raise the frame of the trailer and the overall height of the trailer to a height that would exceeded DOT restrictions. Using four axles, the mobility of the facility would be greatly reduced. Accordingly, the preferred number of axles is three, each rated at 12,000 pounds. In alternative embodiments, the base vehicle may be a motor vehicle such as a bus or a van. Still other embodiments may house the AHRF in a standard intermodal freight transport or shipping container that is compatible with a variety of base vehicles. Although road transport of the AHRF is primarily envisioned, other modes of transportation may be employed in alternative embodiments. For example, platforms such as barges or boats, aircraft, railroad cars, or the like may, serve as base vehicles for the AHRF.

AHRF 100 includes an exterior surface (not specifically illustrated) made of a lightweight, weather resistant material, such as aluminum sheet, and which has as few seams as possible. Aluminum is preferred as an exterior material since it lightweight, cost-effective, weather resistant, and available in a variety of colors. Other similar materials such as a composite, plastic, galvanized sheet metal or stainless steel may likewise be used.

AHRF 100 has an interior floor 106 that provides a monolithic, anti-slip surface, and is chemically resistant throughout. To provide such a surface, floor 106 is preferably made from several layers. Floor 106 includes a layer of plywood and/or aluminum sheet covered with a monolithic troweled epoxy coating floor finish. Floor 106 also includes an integrated coved edge with a 4-in baseboard. The coved edge, with minimum 4-in baseboard provides a seamless surface to help capture and contain any liquid spills and facilitate decontamination and complies with criteria stated for a BSL-3 laboratory. Alternatively, a spray-on coating that is applied to plywood and/or aluminum sheets and has a coved edge with a 4-in baseboard may be used for a floor surface. Although this option provides monolithic and slip resistant flooring as well as more flexibility than the troweled epoxy, which is ideal for a mobile platform, the spray-on coating may have inconsistencies in the thickness of the material. A "bubbling" effect may also appear where the coating does not adhere well to the surface it was sprayed onto.

Interior walls for AHRF 100 (not specifically illustrated) are preferably made from an Oriented Strand Board (OSB) sheathing over standard 16 inch on center studs. Although if fire retardant materials are required, walls could be constructed of metal studs and gypsum. The Interior walls are covered on the inside by solid and smooth Fiber Reinforced Panels (FRP). FRP is available in large continuous rolls that are 8 ft wide, and is easily installed by laying a continuous piece above a 7/16-in OSB sheathing. This process significantly reduces the number of seams and is an ideal material to construct a smooth and impervious wall for a laboratory area that requires easy-to-clean surfaces.

The interior ceiling (not specifically illustrated) of AHRF 100 is also covered with FRP to maintain continuity with the interior walls. Aluminum angle may be used to join sections of FRP together to create a seamless ceiling for easy cleaning and decontamination. Using materials for the walls and ceiling that are easy to clean and easy to chemically disinfect is recommended in the BMBL for a BSL-3 Laboratory.

Electrical Power Systems

Power requirements for the preferred embodiment of AHRF 100 are 300 Amps, 208 Volts, 3-Phase. A main electrical panel 120 is located in a HVAC/Filtration room 109 located in the rear of AHRF 100. An automatic power transfer switch box 122 is located on the exterior rear of the trailer and provides an external point of connection for standard 208 volt 3-phase shore power and generator power. A relatively large electrical system is called for to supply two separate heating, ventilating and air conditioning systems, an AAON 5-ton HVAC single pass unit 170 using 3-Phase power 100 Amps, and a BARD 2.5 ton recirculating HVAC unit 172 using single phase power 60 Amps. A 200 Amp single phase subpanel 124 is located in a BSL-2 Area 105 of the facility to provide easy access to circuit breakers.

Figure 3:
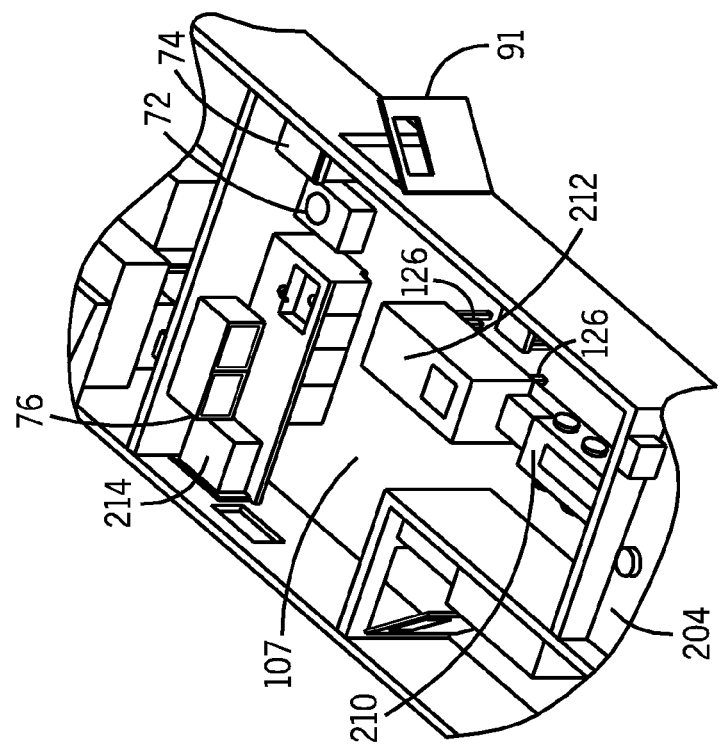
FIG. 3 shows a perspective view of the BSL-3 area of a preferred embodiment of a mobile hazards receipt facility according to the present invention.
Figure 2:
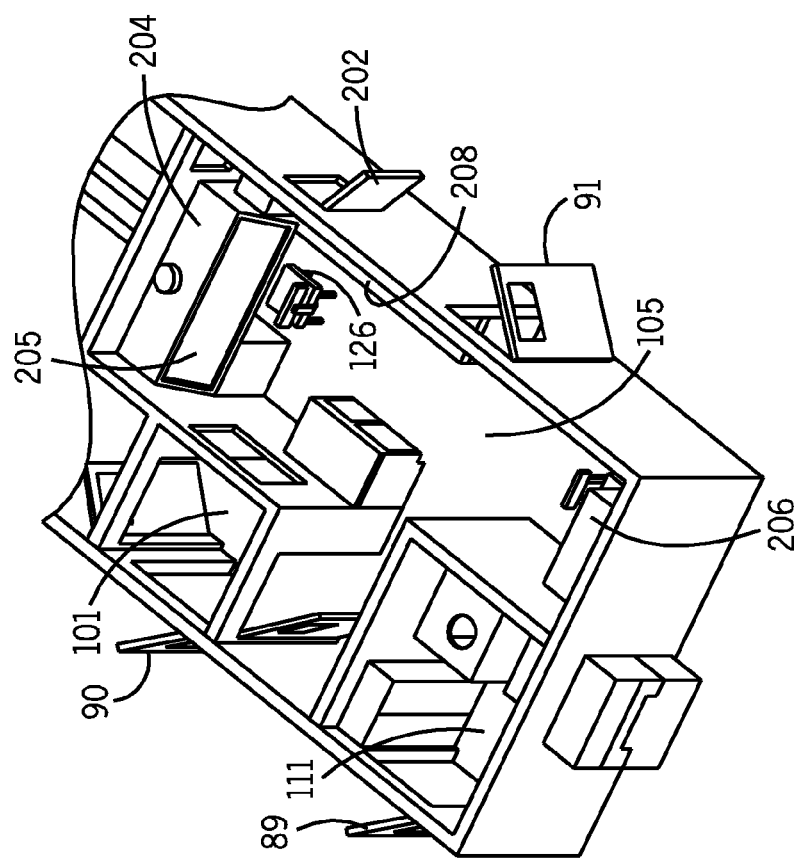
FIG. 2 shows a perspective view of the BSL-2 area of a preferred embodiment of a mobile hazards receipt facility according to the present invention.

As a safety feature, critical systems, for which an unexpected power loss could result in an immediate safety hazard, are connected to one or more Uninterruptible Power Supply (UPS) systems 126 (typical locations shown in FIGS. 2 and 3). For example, containment systems such as gloveboxes and biosafety cabinets should be connected to a UPS. While separate UPS systems 126 for each, unit needing backup power are preferred for robustness and redundancy, a shared UPS power supply system may be employed in alternative embodiments. Each UPS system 126 preferably provides at least 20-30 minutes of back up power, depending on load/consumption, which should allow laboratory personnel enough time to decontaminate and cease operations in ease of a power failure until generator power is activated.

An outboard generator for extended power backup (not illustrated) such as a trailer-mounted 110 kW diesel generator with a 300-gallon fuel tank may also be provided in some alternative embodiments. Power transfer switch 122 should be configured to match the output of any outboard generator. Power transfer switch 122 should also allow for remote operations and monitoring options and be able to automatically start the generator in the event external power is lost.

HVAC

In general, an HVAC system for a containment area should provide thermal comfort, acceptable indoor air quality, ventilation, air filtration, and maintain air pressure relationships between spaces. There are two separate Heating, Ventilating, and Air Conditioning (HVAC) units for AHRF 100. The larger HVAC is a 5-ton split single-pass unit 170 (AAON), located in a HVAC/Filtration Room 109 that is sealed off from the laboratory areas of AHRF 100. The other HVAC unit is a 2.5-ton recirculating unit 172 (Bard) located outside of utility room 111 on the opposite end of AHRF 100 which is also sealed off from the AHRF 100 laboratory areas. The single-pass unit 170 provides the BSL-3 Area 107 and changeroom 103 with single pass air to fulfill the safety requirements for dealing with unknowns. Single-pass unit 170 is manufactured by AAON, Inc. and was selected due to its physical size, air handling capacity, electrical requirements and cost. By dividing AHRF 100 into BSL-2 and BSL-3 areas the electrical requirements, physical size and overall cost of the single pass HVAC needed for a BSL-3 laboratory may be significantly reduced.

Water

In general, the water supply for an embodiment of an AHRF according to the present invention must be adequate to meet the needs of all routine laboratory operations and also be able to rapidly deliver a large volume of water to safety showers and eyewash stations in emergencies. Wastewater from the safety showers is stored in sealed holding tanks 219, under floor 106 and separate from sink holding tanks 221.

The water supply connection for AHRF 100 is a standard external hose connection (not shown) that directly fills a large onboard potable water tank 220 in utility room 111, preferably having a capacity of at least 100 gals. The option to have a tank bypass, thereby a demand pump bypass, for a direct city connection is not a good choice since city water pressure typically would not be adequate to force the emergency safety shower at a satisfactory flow. A demand pump 242 in utility room 111 supplies water to AHRF 100 from water tank 220. Demand pump 242 should be able to deliver sufficient pressure and volume as required for safety showers 214, which are located beside each emergency exit 216. Back up power should be provided to demand pump 214 to ensure that the water supply is not interrupted in the event of a power failure.

Three sinks 218 are preferably provided in AHRF 100. Sinks 218 include foot pedals to enable hands free operation, as recommended by the BMBL. While automatic sinks may also be used, foot pedal operation sinks are generally more reliable and easier to repair in the field than automatically operated sinks. Each sink location also includes an instant hot water heater (not illustrated), which eliminates the need for a hot water tank. Emergency eye wash stations 222 are located at each sink 218 in the BSL-2 and BSL-3 Areas area.

Tank heaters (not illustrated) are another feature incorporated into AFIRE 100 so that during freezing temperatures, they may be turned on to automatically keep all holding tanks from freezing. A level indicator and alarm is also present for all holding tanks, potable and waste, to notify laboratory personnel if potable water is running low or any waste tanks need to be emptied by a septic or waste pump out service.

Onboard waste holding tanks 221 are included onboard AHRF 100 and are positioned beneath the floor directly under the emergency showers. In some instances, the waste tanks may be directly connected to a sewer line. If there is a chance that any hazardous substances could be present in the waste tanks, precautions must be taken to ensure that the waste is properly disposed, During field deployments, where a constant source of fresh water may not be available, the level of the water in potable water tank 220 must be checked daily before laboratory operations begin. The water supply for the eyewash stations, the safety showers, and any other use comes from the same source. If the water level in the potable holding tanks is too low, there may not be enough supply to effectively operate the eye washes and safety showers. Preferably, potable water tank 220 is equipped with a water level indicator and/or a low level alarm such as an indicator light to ensure that the potable tank 220 is filled to the proper level before operations begin and is refilled as necessary.

AHRF Entrances, Exits and Interior Doors

AHRF 100 includes a main entrance 90, a utility room entrance 89, a double door entrance 93 to an HVAC filtration room 109 and two emergency exit doors 91. In general, each entry door is double O-ring sealed and each is equipped with a cipher lock, or similar, to prevent unauthorized entry. A first entry door 90 is located in anteroom 101 and is used as the primary point of ingress and egress for AHRF personnel. A second entry door 89 is provided for direct access from the outside into utility room 111 which is isolated from the rest of AHRF 100. A third double door entry 93 is provided into HVAC/Filtration Room 109 which is also isolated from the rest of AHRF 100 Laboratory area.

As shown in FIG. 1, sample exit pass-through double air-lock doors are also included in AHRF 100. A Double Door Airlock 214 is provided into High Containment BSL-3 Area 107. Exterior Intercom Stations are positioned beside both the entrance door 90 and the sample exit pass-thru 214 to allow laboratory personnel to communicate from within the trailer to outside. Security Cameras 84 are in place beside Sample exit Pass-thru Door 214 and entrance door 90 to monitor and record all activity. Exterior Lights are also mounted near each exit to provide illumination.

In general, all doors in the interior of AHRF 100 are double O-ring sealed in order to provide an air tight seal when the doors are closed. This feature facilitates control of the airflow and pressure differentials within the AHRF and maintains a functioning laboratory in the field.

The main entrance door is electrically/magnetically interlocked. The sample entry pass-through and the exit passthrough also use electrically/magnetically interlocking doors.

AHRF Layout

The interior layout of the AHRF is designed to facilitate sample flow, primary containment, and secondary containment so that an unknown sample need never leave a primary containment unit and the interior of the entire AHRF platform until triage has been performed to determine the hazard associated with the sample. The sample flow within the AHRF is discussed in detail below. The interior layout is also designed to allow three to five laboratory personnel to work comfortably inside the facility and to still have all the necessary utility equipment housed within the platform. The interior design concept of the AHRF is shown in FIGS. 1-3.

Anteroom

Anteroom 101 provides the main entrance 90 into the AHRF and is located on the curb side of the trailer. Anteroom 101 is separated from other laboratory areas by self-closing doors, as recommended in the BMBL, and provides a first self-closing door 92 (on the right) that leads to an adjacent Receiving-Log-in/BSL-2 Area 105 and a second self-closing door 94 (on the left) that leads to an adjacent change room 103. Across from main entrance 90 of anteroom 101 is a viewing window 95 into Receiving-Log-in/BSL-2 Area 105. Anteroom (Main Entrance) 101 is maintained at a positive pressure of +0.10 in. water gauge (wg) with respect to the air outside the AHRF.

Change Room

Change room 103 provides benches and lockers so that laboratory personnel are able to change into the appropriate laboratory attire before entering into the BSL-3 Area of AHRF 100. Change room 103 is also at a pressure of −0.10 in. wg with respect to the outside. A cabinet 80 in change room 103 houses a recording apparatus 82 (the server) for a camera system 84. At the far end of change room 103 opposite self-closing door 94 is another self-closing door 96 leading to a High Containment or BSL-3 Area 107. The self-closing doors on either end of change room 103 are electrically/magnetically interlocked.

BSL-2

As noted, Receiving Log-in/BSL-2 Area 105 is on the right upon entering anteroom 101, Self-closing door 92 from anteroom 101 into receiving log-in/BSL-2 105 is also electrically/magnetically interlocked with main entrance door 90. The interlocked doors are used to help maintain the air pressure in each section. All interior doors have wire-reinforced half-glass windows for viewing as recommended by the Anthology of BioSafety VII, BSL-3 (see page 22).

Bleaching Station

Primary containment for samples in Receiving-Log-in/BSL-2 Area 105 is provided by a Bleaching Station 204. Sample entry is permitted on the street side of the trailer through an interlocking double door airlock 202 that leads directly into Bleaching Station 204. Bleaching station 204 is an elongate rectangular cabinet providing an interior work space approximately 77 in wide and 28 in deep. An angled transparent glass or polycarbonate front panel 205 that is detent or friction hinged at the top enables adjustable operating clearance and proper containment. The open-faced design of bleaching station 204 is preferable to the confines of a more restrictive enclosure such as a glovebox because the operator's ability to handle incoming sample containers is significantly improved and the level of containment is more appropriate to the work being performed. Bleaching Station 204 is preferably constructed of welded 316 stainless steel. The interior surfaces are coated with a Halar® finish, or similar material, to provide protection from highly corrosive decontamination solutions. An interior light is provided for the work area.

Bleaching Station 204 is designed to extract any vapors that may emanate from incoming sample packages and draw particulates away from the operator and laboratory and towards the back wall of the work space within. A drain is located on one end of bleaching station 204 and sinks 218 are connected to onboard waste holding tanks 221. The interior work area of bleaching station 204 is sloped towards the drain to dispose of any liquids. Bleaching station 204 also provides an enclosed hood with adjustable airflow baffles on the back wall so that the airflow may be adjusted by laboratory personnel.

BSL-2 Area 105 also includes a Computer Workstation 206 to log in samples and perform any chain-of-custody documentation when samples enter this laboratory area via Bleaching Station 204, BSL-2 Area 105 also includes a workbench 208, preferably located adjacent to Bleaching Station 204. While other cabinets and countertops within AHRF are generally made of stainless steel, workbench 208 is provided with a very durable, heat and chemical resistant countertop of a stone-like material such as Corian® or similar, and is equipped with a hands-free sink and an eye wash station. Receiving-Log-in/BSL-2 Area 105 is maintained at a negative pressure of −0.10 in wg with respect to the outside.

BSL-3 Area

High Containment/BSL-3 Area 107 includes an emergency eye wash and safety shower station 70 beside an emergency exit door 91 on the street side of the trailer. A second emergency eye wash and shower station 70 is located next to emergency exit door 91 from the Receiving-Log-in/BSL-2 Area 105.

An autoclave 72 is also available in High Containment/BSL-3 Area 107 to sterilize any necessary items. Having autoclave 72 in the BSL-3 Area also provides a means of decontaminating laboratory waste in AHRF 100. This is recommended in the BMBL (p34) as part of the facilities for a BSL-3 laboratory.

The primary containment for samples in BSL-3 107 Area is a Double-Sided Class III Glovebox 210 for performing triage (i.e., for determining how a sample will be further handled) and Biosafety Cabinet 212. Glovebox 210 provides a secure environment to open the sample containment and perform preliminary testing. A Chemical Biological Radioactive (CBR) Exhaust Air Filtration system 178 is also provided for Glovebox 210 to ensure proper containment of chemical, biological, and radioactive warfare agents. A Double-Sided Class III Biosafety Cabinet (Glovebox) with CBR Exhaust Air Filtration System is defined in the BMBL (see p, 202) as a "totally enclosed, ventilated cabinet, . . . , and offers the highest degree of personnel and environmental protection" from biological and chemical hazards. The filtration system consists of both ASZM-TEDA carbon filters and NEPA filters to capture any possible chemical and/or any possible biological hazards. In general, a glovebox with CBR filtration is provided at this stage as the primary containment unit due to the high level of protection needed for opening a primary sample container that encloses an unknown sample. Glovebox 210 is preferably double-sided with three glove ports on each side to allow the laboratory operators to work simultaneously from both sides in situations where difficult procedures are required for handling samples.

Glovebox 210 is preferably constructed of all welded 12 and 16 gauge 316 Stainless Steel which is polished to a 180-grit pharmaceutical grade (#4) finish to allow for easy cleaning and decontamination. Glovebox 210 also includes viewing panels constructed of 3 ⅛-in thick polycarbonate and provides three oval Stainless Steel double grooved gloveports which allow for changing the butyl gloves without breaking containment. Butyl gloves are preferably 32 in. long with a 15-mil thickness, and are held in place with two rubber O-rings. Glovebox 210 also includes a control panel that displays the pressure inside in digital and analog formats as well providing audible and visual low-pressure alarms to alert personnel when containment pressure is inadequate. Glovebox 210 is connected to a 15-amp dedicated circuit for its primary power supply and has two sealed electrical receptacles located inside the glovebox.

Glovebox 210 is connected via a quad door airlock to Class II A2 Biosafety Cabinet 212 to allow laboratory personnel to conduct further biological testing of a sample that may contain biohazardous materials, as may be required. Biosafety Cabinet 212 is, essentially, a standard 4-ft Biosafety Cabinet and provides an area for further biological laboratory work, if needed, as well as an area for over packing the sample for transport to the main laboratory or another facility. A biosafety cabinet has been chosen since chemical or radiological samples will be processed in glovebox 210 and only samples appropriate for further biological work will be moved on to biosafety cabinet 212.

Biosafety Cabinet 212 is made from welded 304 Stainless Steel with a #4 pharmaceutical grade finish. The front panel is ergonomically designed with a concave face to permit the operator to lean into the work area thereby reducing strain. A removable Stainless Steel work tray, which is 47 in. wide by 16¼ in deep, allows easier cleaning. Fluorescent lights are mounted on the exterior of Biosafety Cabinet 212 to illuminate the work area within and minimize heat build-up. Changing of HEPA filters for Biosafety Cabinet 212 may be changed or otherwise accessed from the rear of Biosafety Cabinet 212.

High Containment/BSL-3 Area 107 also has a refrigerator/freezer 74 and a flammable cabinet 76 under the counter. A double door airlock 214 is provided in High Containment/BSL-3 Area 107 on the curbside of the trailer for removing samples from AHRF 100.

HVAC/Filtration Room

HVAC/Filtration room 109 houses the Aaon 5 ton HVAC Single Pass unit 170, which is equipped with a HEPA booster 171, as well as the filtration components for all the primary containment units: Bleaching Station 204, Class III BSC (Glovebox) 210, and Biosafety Cabinet 212. Keeping this filtration and ventilation equipment separate from the main laboratory areas allows for maintenance to be performed in a centralized area and reduces the noise level in the laboratories. HVAC/Filtration room 109 is accessible from the rear of AHRF 100 via a set of double doors 93.

A rollup door 167 on the street side of the trailer provides access to the bag in bag out (BIBO) HEPA carbon filtered hood exhaust unit 174 and facilitates changing of filters using the Bag in/Bag out procedure, A double door 168 is provided on the curbside of the trailer for the same purpose for the room breathing air filtration and exhaust system 173.

Utility Room

A Utility Room 111 is located on the curbside of AHRF 100, towards the front of the trailer. Utility Room 111 houses a HEPA/carbon filter and booster blower 169 for the 2.5-Ton recirculating HVAC unit 172, a variable frequency drive for the 2.5-Ton recirculating HVAC unit 172, demand water pump 242, and the 100-gallon potable water holding tank 220. The utility room 111 is sealed off from the BSL-2 Area so it is not accessible from inside AHRF 100. An exterior door 89 provides entry into Utility Room 111.

Airflow Through the AHRF

Figure 4:
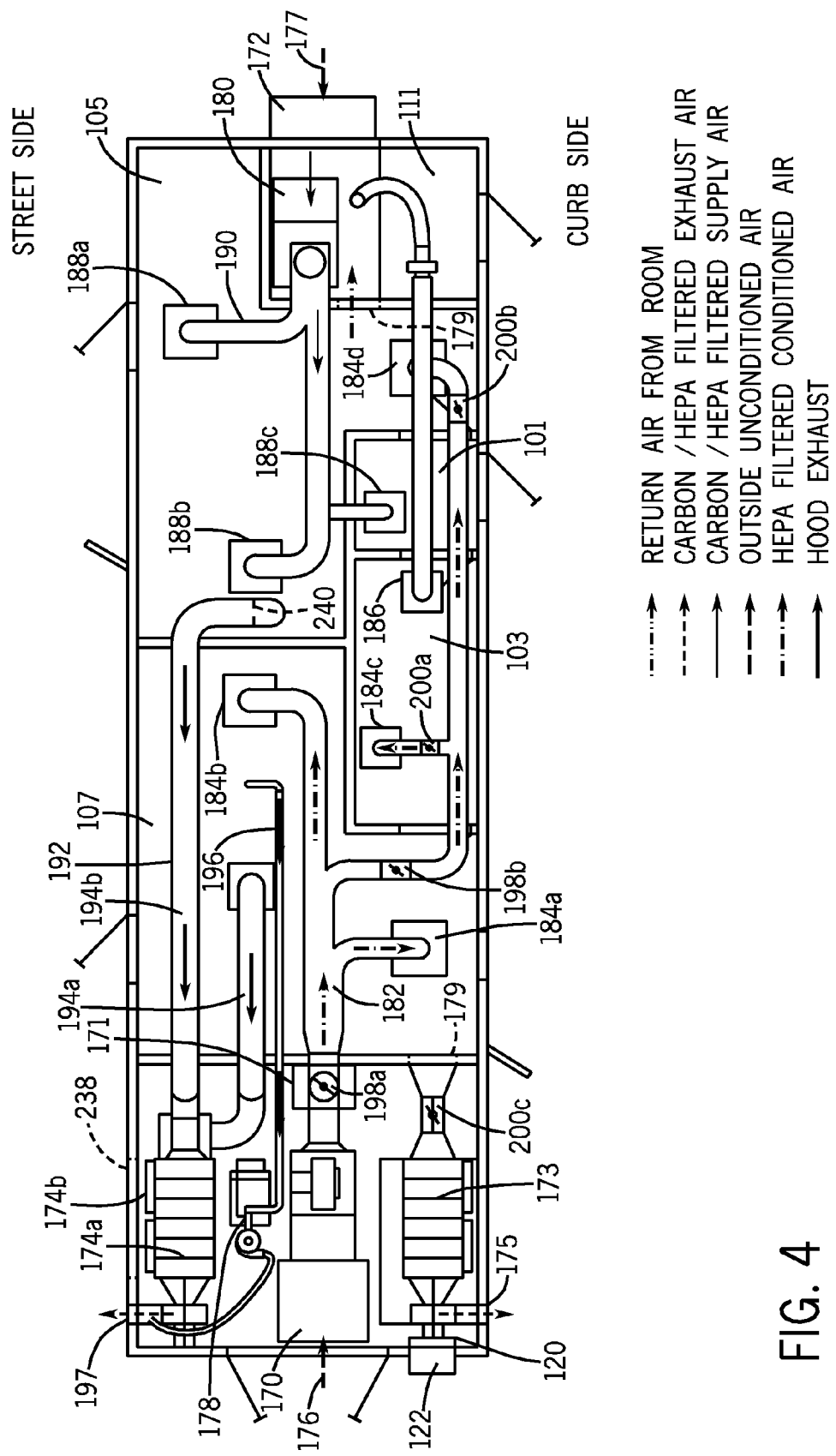
FIG. 4 shows a schematic of the airflow through a preferred embodiment of a mobile hazards receipt facility according to the present invention.

FIG. 4 shows a diagram of airflow through AHRF 100 and Table 2 lists preferred airflow specifications. In general, AHRF 100 is designed to provide a continuous and inwardly directed airflow at all times when the lab is in operation. Inward airflow is assured by monitoring and maintaining appropriate pressure differentials to ensure that air always flows towards areas of higher containment. This is accomplished essentially as follows. Single pass HVAC unit 170 draws outside air continuously through an air intake port 176 located in the back wall of HVAC/Filtration Room 109. This airflow is HEPA filtered before it is conveyed through an overhead single pass duct 182 to air supply outlet vents 184*a*, 184*b*, 184*c* and 184*d*. Air supply outlet vents 184*a* and 184*b* are located in the BSL-3 Area 107. Air supply outlet vent 184*c* is located in change room 103 and air supply outlet vent 184*d* in BSL-2 Area 105. HEPA filtration of intake air ensures that any hazardous microbial airborne particulates in the outside air are removed before air is circulated in AHRF 100.

A second air supply is provided by recirculating HVAC unit 172. Recirculating HVAC unit 172 is located outside utility room 111 but is substantially sealed off from utility room 111. Recirculating HVAC unit 172 recirculates air from inside AHRF 100 and mixes it with fresh air from the outside. Outside air is drawn from an air intake port 177 located in the HVAC unit 172 and from air supply vent 184*d*. Inside air is drawn through a grating 179 through an adjacent inside wall which opens into BSL-2 Area 105, and from a return duct 186 which runs from change room 103 directly into Recirculating HVAC unit 172. Airflow from Recirculating HVAC unit 172 is HEPA and carbon filtered in a recirculating filtration unit 180 which is equipped with a booster fan before it is conveyed through an overhead duct 190 to recirculated air supply outlet vents 188*a*, 188*b* and 188*e*. Recirculated air supply outlet vents 188*a* and 188*b* are located in BSL-2 Area 105 and Recirculated air supply outlet vent 188*c* is located in anteroom 101. An air return is not generally needed in anteroom 101 because it is maintained at a positive pressure.

The HVAC system for AHRF 100 is equipped with bioseal dampers 198a and 198b which are positioned in single pass HVAC system supply duct and function as automatic check valves to ensure that contaminated air cannot be backdrafted through the ducts in the event of a system failure. TSI dampers 200a, 200b and 200c are located in single pass HVAC supply/return ducts and enable automatic pressure adjustment and airflow control in BSL-2, BSL-3 and change room areas. Additional dampers and flow modulators may be provided in other branches of the HVAC system, as needed, to further control airflow and to maintain appropriate pressure differentials.

Several dedicated exhaust and HEPA carbon filtration systems are also provided in HVAC/filtration room 109. A glovebox filtration system 178 provides exhaust and HEPA carbon filtration for Glovebox 210 via a glovebox duct 196. BI-BO HEPA carbon filtered hood exhaust systems 174a and 174b provide exhaust and HEPA carbon filtration for Biosafety Cabinet 212 and Bleaching Station 204, respectively, via a biosafety cabinet duct 194a and bleaching station duct 194b. Return air from High Containment/BSL-3 Area 107 passes through HEPA carbon room filtration and exhaust unit 173 before being exhausted at HEPA carbon room filtration exhaust outlet port 175.

Color Coding and Labeling

An additional feature of AHRF 100 is a color coding scheme to insure that samples, supplies and equipment are located in the areas where they should be. In the BSL-2 Area 105, for example, the labels are yellow with black text. In Change room 103, the labels are green with white text. In BSL-3 Area 107, the labels are red with white text. Other colors and labeling schemes may likewise be employed. Additionally, in some environments, it may be desirable to include magnetic or electronic transponders to trigger an alarm when objects are moved from area to area without authorization.

Sample Movement and Primary Containment

Samples typically will arrive at the AHRF 100 in some form of protective packaging. Standard protocol calls for arriving samples to be contained in an airtight primary sample container that is covered by a secondary protective overpack. Although the risk of contamination is low, all incoming sample containers will be decontaminated.

Samples are initially received on the street side of AHRF 100 through an interlocking double-door airlock 202. Double-door airlock 202 preferably provides a 16 in. wide by 16 in. high opening and is secured with a cipher lock, or similar, for keyless entry. An intercom is also preferably provided near double-door airlock 202 to facilitate communication with personnel inside the AHRF when samples are delivered. A "two-man entry rule" should be followed when accepting unknown samples to ensure that samples are only processed into the AHRF when another person is inside the facility and knowingly accepts the sample. Double door airlock 202 is positioned so that samples entering AHRF 100 are passed directly into the specially designed Bleaching Station 204 in BSL-2 Area 105.

In operation, a sample container is received through double door airlock 202 and is moved directly into bleaching station 204 through a common sidewall. A prescribed quantity of liquid decontamination solution (such as household bleach) is applied to the secondary over pack of a sample after it is moved inside bleaching station 204. The sample overpack may be wiped down with bleach, rinsed, and then removed to expose the primary sample container. The bleaching and rinsing process is then repeated on the primary sample container to ensure that there are no hazards on the exterior.

The back wall of Bleaching Station 204 is integrated with an interlocking double-door air-lock that leads to the Class UI Glovebox 210 located in BSL-3 Area 107. The double-door air-lock between bleaching station 204 and glovebox 210 is provided to prevent the sample from leaving any environmental enclosure and possibly contaminating the laboratory.

Once triage has been performed within glovebox 210, the sample may be moved through an interlocking quadruple door airlock leading from glovebox 210 to Biosafety Cabinet 212. Biosafety Cabinet 212 provides a work area for further biological laboratory work, if needed, as well as an area for over-packing the sample for transport to another facility.

After the sample has been prescreened, triaged, and packaged or repackaged in BSL-3 Area 107, the sample may be placed into a sample exit/pass through Double Door Interlocking Airlock 214 located on the curb side in BSL-3 Area 107. The contained sample can then be removed from the facility for transport to a fixed-site laboratory for further testing or other appropriate processing.

Electronic and Computer Systems

In order to provide communications to AHRF 100, external phone and data ports are provided so that the phone lines and data ports located throughout the inside of the facility can be easily connected and activated. For data lines inside AHRF 100, a network router is provided so that the interior of the facility may be networked and connected to the internet. Another feature, included for security purposes, is a camera system that has a server that may be connected to the internet if it is available. This features allows remote users to view the security cameras to the facility over the internet. The security camera system is discussed in the next section.

Security and Closed Circuit TV System

There are preferably eight security cameras 84 connected to a server 82 that stores video recorded from the cameras. Four cameras 84 are installed on the exterior of the AHRF to monitor the entrance door, sample entrance, sample exit, and the emergency exit doors. There are also two cameras 84 in BSL-3 Area 107, one in BSL-2 Area 105 and an additional "bullet" camera with a focal length suited to view the operations within glovebox 210. At least three flat screen monitors allow laboratory personnel to view all the cameras throughout the AHRF. The server may be programmed to automatically record each camera's view for approximately 15-30 days depending on the video quality. Using a router, the server may be networked for remote access via a local or wide area network such as the internet and also to enable voice over internet protocol and data communications. A variety of access permissions may be set for users and administrators thereby safeguarding access and control functions for video surveillance and communications systems.

Although a less expensive video surveillance system may be provided, the safety and security of AHRF 100 personnel are better served by a video surveillance system that provides good image quality, adequate coverage inside and outside of AHRF 100, extensive video recording capability, internet access, restricted access and the capability to serve multiple users, remote administration and the ability to replace hardware components such as the cameras and server easily if any problems should occur.

Intercom System

An intercom system with four internal hands-free master stations 236 and three external door stations 237, allows laboratory personnel to speak to persons at the main entrance, sample entrance and exit as well as between rooms. Door release buttons are also located by each master station 236 to remotely release doors to allow entrance into the AHRF and to open the sample entrance and sample exit pass through doors. An intercom system was chosen to facilitate communications between laboratory personnel both within the AHRF and with those outside the facility.

Fire Alarm and Smoke Detectors

Throughout the AHRF are five smoke detectors with a 135° rate of heat rise detector, three fire alarm pull stations and two horn/strobes. There is also a fire panel that has two zones with controls to silence and reset the system. One zone is to handle the BSL-2 area and utility room and the other zone is to handle the BSL-3 area, change room and the HVAC/filtration room. The fire alarm pull stations activate a horn/strobe inside the trailer and a horn/strobe on the exterior. A relay contact is provided for integration to an exterior building fire alarm system. The fire alarm was specifically requested by the customer. While a sprinkler system could be installed in the AHRF it would significantly increase the cost of construction due to the installation of the necessary plumbing and fixtures as well as mounting a separate water holding source with water pump system separate from the potable holding tank and demand pump. Moreover, the components necessary for a sprinkler system would also take up valuable space in an already confined area. Emergency measures are designed into the platform of the AHRF in case there is a fire: emergency exits 91 were placed in each of the laboratory rooms to allow personnel to exit quickly. In addition, fire extinguishers are available throughout the facility.

Site Preparation

After a site assessment has been performed, depending on the mission and available funds, the next step is site preparation. This could include clearing space, possibly paving the area, installation of an electrical pole, and running underground cable. Depending on the need for an onsite city water connection, underground plumbing may also need to be installed at the site.

CONCLUSION

As has been shown, embodiments according to the present invention provide a mobile all hazards receipt facility. A number of embodiments of the invention defined by the following claims have been described. Nevertheless, it will be understood that various modifications to the described embodiments may be made without departing from the spirit and scope of the claimed invention. Accordingly, other embodiments are within the scope of the invention, which is limited only by the following claims.

TABLE 1

Physical Characteristics of Preferred Embodiment

| Item | Specifications |
| --- | --- |
| Size | 48 ft (L) × 13 ft 9 in (W) × 13 ft 6 in (H) |
| Approximate Weight | 45,000 lb |

TABLE 1-continued

Physical Characteristics of Preferred Embodiment

| Item | Specifications |
| --- | --- |
| Exterior Siding & Trim | 0.19 Aluminum siding<br>0.19 Aluminum trim at top, bottom, corners<br>Sheathing of 7/16 in. OSB w/Tyvek Housewrap |
| Frame | 3-12,000 lb axles<br>Alloy rims, truck tires, and electric brakes<br>12 in Main Beam perimeter<br>Cross member 13-gauge formed steel 48 in on center |
| Flooring | Floor joist are 2 × 6 wood studs<br>Decking above joist is double layer 3/4-in. plywood<br>Insulation 6 in. R-19<br>Finished flooring is trowel epoxy coating w/integrated 4 in coved base. |
| Walls | Studs 2 × 4 in, 16 in on center, 8 ft high<br>Insulation R-11 Kraft-faced F/G<br>Sheathing of 7/16 in OSB<br>Covering is 0.085 smooth "white" Fiber Reinforced Panels (FRP) |
| Interior Trim | Corners and wall to ceiling with "white" aluminum angle<br>Interior doors painted hollow metal frames |
| Roof System | Roof Trusses 16 in on center spacing<br>Sheathing of 7/16 in. OSB<br>Covering 0.045 EPDM "black" rubber<br>Insulation of 6 in R-19 Kraft-faced<br>Interior Ceiling of 0.085 smooth "white" FRP bonded to 1/2 in plywood |
| Towing | Removable bolt-on ball hitch<br>Recommended tow vehicle is tractor trailer with ball hitch connection |
| Electrical | 300 Amp with a 200 Amp Subpanel,<br>120/208 Volt, Three-Phase, 4-Wire |
| HVAC | Bard 2.5-Ton HVAC unit<br>HEPA/Carbon booster<br>Thermostat is 7-Day programmable heat/cool<br>Aaon 5-Ton Single Pass Air<br>HEPA booster with Stainless Steel Bioseal damper<br>Supply and return air ductwork is galvanized<br>Stainless steel adjustable dampers, 6 in, 8 in, 10 in with controllers |
| Water System | Supply has CPVC pipe and fittings w/water pump for 100 gal supply holding tank<br>Waste has SCH 40 PVC pipe and fittings with three water tanks mounted below frame<br>Sinks are Stainless Steel mounted in furniture |

TABLE 2

HVAC Air Flow Specifications of Preferred Embodiment

| Room/Area | Volume (ft³) | Supply Air (CFM) | Room Air Changes/hr | Outside Air Changes/hr | Pressure with Respect to the Outside(WG) |
| --- | --- | --- | --- | --- | --- |
| Anteroom | 164 | 100 | 37 | — | +0.1 |
| Change Room | 355 | 180 | — | 30 | −0.1 |
| BSL-2 | 1118 | 1170 | 63 | 10 | −0.1 |
| BSL-3 | 1349 | 730 | — | 32 | −0.25 |

What is claimed is:

1. A mobile hazards receipt analytical laboratory, comprising:
a substantially sealed enclosure adapted for mounting on a base vehicle, said enclosure for containing laboratory equipment and personnel, the enclosure comprising a plurality of sealed outside entries that can be locked to prevent unauthorized access, the enclosure further comprising the following:
an anteroom wherein the air is maintained at a pressure that is greater than about +0.10 inches of water gauge (in wg)

with respect to the outside air and that leads to at least one other room in the laboratory and comprises a main outside entry for personnel;

a containment area compliant with BioSafety Level-2 (BSL-2) standards, wherein the air is maintained at a pressure that is less than about −0.10 in wg with respect to the outside air and which is directly accessible from the anteroom;

a change room wherein the air is maintained at a pressure that is less than about −0.10 in wg with respect to the outside air and which is directly accessible from the anteroom;

a containment area compliant with BSL-3 standards wherein the air is maintained at a pressure that is less than about −0.25 in wg with respect to the outside air and which is directly accessible from the change room;

a bleaching station located in the BSL-2 area, the bleaching station comprising a partially enclosed work area for application of a decontamination solution to sample containers, wherein said bleaching station further comprises a REPA and carbon filtered exhaust system and wherein said bleaching station includes an airlock to the outside through which samples can enter the laboratory;

a double-sided class III glovebox located in the BSL-3 area, the glovebox including a Chemical Biological Radiological (CBR) exhaust air filtration system;

two independent interlocked airlocks, one through which samples may be passed directly from the bleaching station in the BSL-2 area into the glovebox in the BSL-3 area, and the other through which samples may be passed from the glovebox into a biosafety cabinet in the BSL-3 area; and an interlocked airlock in the BSL-3 area to pass samples out of the laboratory.

2. The mobile hazards receipt analytical laboratory according to claim 1, wherein the air inside the laboratory is filtered, conditioned, and maintained to BSL-2 and BSL-3 standards by an on-board air handling system.

3. The mobile hazards receipt analytical laboratory according to claim 1, wherein the substantially sealed enclosure comprises a standard intermodal freight transport or similar shipping container that is compatible with a plurality of base vehicles.

4. The mobile hazards receipt analytical laboratory according to claim 1, wherein the base vehicle comprises a wheeled semi-trailer transportable over roads including the U.S. Interstate Highway System.

5. The mobile hazards receipt analytical laboratory according to claim 1, wherein accesses from the anteroom to adjacent areas comprise doors that are electrically/magnetically locking and self-closing.

6. The mobile hazards receipt analytical laboratory according to claim 1, wherein the glovebox includes glove ports on opposite sides.

7. The mobile hazards receipt analytical laboratory according to claim 1, wherein access to the anteroom and to the BSL-3 area is provided through magnetically locking, self-closing doors.

8. The mobile hazards receipt analytical laboratory according to claim 1, wherein the bleaching station airlock to the outside through which samples can enter the laboratory comprises an interlocking double-door airlock.

9. The mobile hazards receipt analytical laboratory according to claim 1, further comprising:
a main electrical panel for connection to a primary source of electrical power;
a secondary source of electrical power to supply back up power to a plurality of electrically powered systems in the event of a failure of the primary source of electrical power;
a first HVAC system comprising a single pass unit;
a second HVAC unit comprising a recirculating unit;
a water supply comprising an onboard potable water tank; and
a waste collection tank.

10. The mobile hazards receipt analytical laboratory according to claim 1, further comprising a safety shower and eyewash station.

11. The mobile hazards receipt analytical laboratory according to claim 1, further comprising a surveillance camera system with video recording capability.

12. The mobile hazards receipt analytical laboratory according to claim 1, further comprising a hands-free intercom system for communicating with persons outside the laboratory.

13. The mobile hazards receipt analytical laboratory according to claim 1, further comprising a labeling scheme to indicate areas where laboratory supplies and equipment belong.

* * * * *